(12) United States Patent
Klare et al.

(10) Patent No.: US 8,506,297 B2
(45) Date of Patent: Aug. 13, 2013

(54) DENTAL MODEL

(75) Inventors: Martin Klare, Dortmund (DE); Markus Kaiser, Muenster (DE); Frank Gischer, Menden (DE)

(73) Assignee: DREVE ProDiMed GmbH, Unna (DE)

( * ) Notice: Subject to any disclaimer, the term of this patent is extended or adjusted under 35 U.S.C. 154(b) by 0 days.

(21) Appl. No.: 13/423,321

(22) Filed: Mar. 19, 2012

(65) Prior Publication Data
US 2012/0237903 A1 Sep. 20, 2012

(30) Foreign Application Priority Data

Mar. 18, 2011 (DE) .................... 20 2011 000 623 U
Nov. 26, 2011 (DE) ......................... 10 2011 119 511

(51) Int. Cl.
*A61C 11/00* (2006.01)
(52) U.S. Cl.
USPC .............................................. 433/213
(58) Field of Classification Search
USPC ........... 433/213, 214, 34, 72–76; 264/16–18; 434/264, 263
See application file for complete search history.

(56) References Cited

U.S. PATENT DOCUMENTS

| | | | | |
|---|---|---|---|---|
| 3,498,580 A * | 3/1970 | Wilson | ............................ | 249/54 |
| 3,704,519 A * | 12/1972 | Lystager | ....................... | 433/213 |
| 4,398,884 A * | 8/1983 | Huffman | ........................ | 433/74 |
| 4,767,330 A * | 8/1988 | Burger | ........................... | 433/213 |
| 4,834,651 A * | 5/1989 | Fenick | ............................ | 433/74 |
| 5,788,489 A * | 8/1998 | Huffman | ......................... | 433/60 |
| 7,018,207 B2 * | 3/2006 | Prestipino | .................... | 433/213 |
| 2002/0110786 A1 * | 8/2002 | Dillier | ........................... | 433/213 |
| 2006/0127851 A1 * | 6/2006 | Wen | ................................ | 433/213 |
| 2011/0129800 A1 * | 6/2011 | Marotta | ........................ | 433/213 |

* cited by examiner

*Primary Examiner* — Yogesh Patel
(74) *Attorney, Agent, or Firm* — Andrew Wilford

(57) ABSTRACT

A dental modal for making a dental prosthesis has a base body formed with model teeth and model gingiva and with a cutout in an edentate area and with a hole in a floor of the cutout. A plate is releasably fittable complementarily in the cutout and is formed with a hole aligned with the hole of the cutout. A gingiva mask is fittable on the plate in the cutout and is in turn formed with a hole aligned with the holes of the plate and of the cutout. A model implant insert is releasably fittable in the holes of the mask, plate, and cutout and carries a model implant or an implant-screw mockup.

8 Claims, 1 Drawing Sheet

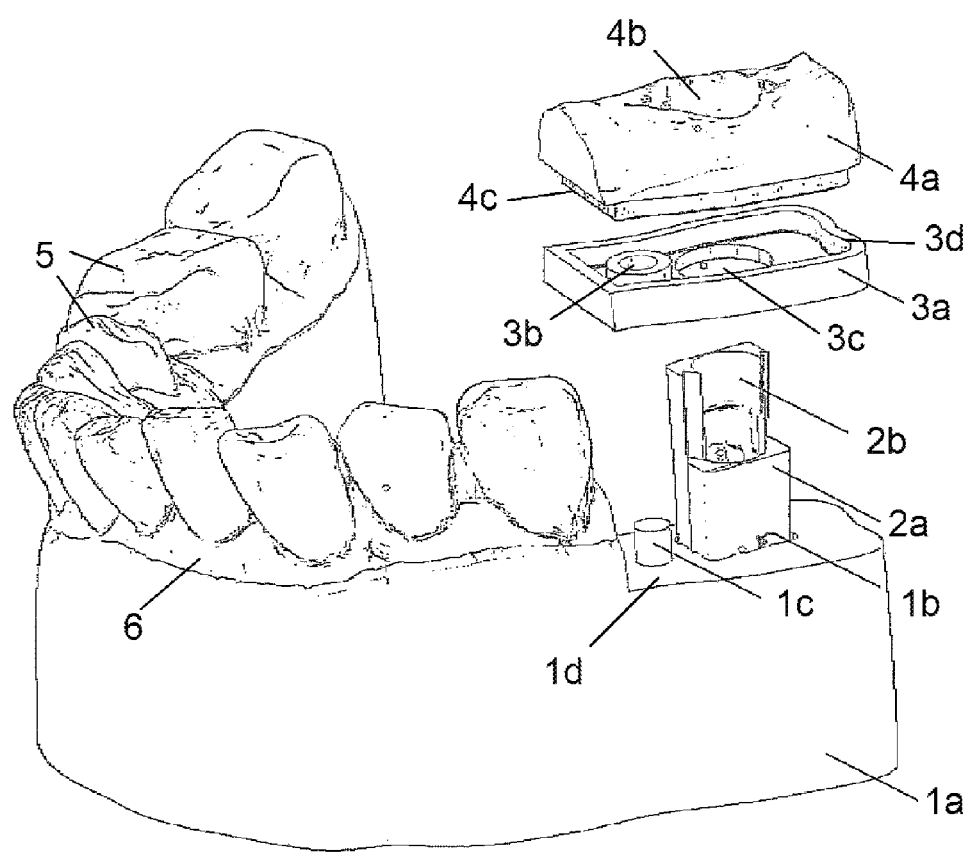

__
DENTAL MODEL

FIELD OF THE INVENTION

The present invention relates to a dental model. More particularly this invention concerns a method of making a dental model.

BACKGROUND OF THE INVENTION

A dental model is typically made generatively as a working and control model for preparing a dental prosthesis and comprises a base with a body and model gingiva and model teeth shaped thereon as well as an area in which a model implant of a tooth or a dental group is to be formed.

Such dental models are typically cast from plaster. Therefore, a dental impression is taken from the patient and a model is prepared after taking the impression, this dental model then serving as a working model and control model for preparing the dental prosthesis. The dental model has an empty spot vacancy in the position where the patient is missing one or more teeth. The dental technician must then model a tooth or teeth at this location on the dental model, and this model must then later be positioned in the patient's mouth and secured there.

It is also known that dental models can be created by so-called generative fabrication where digital data is recorded from a patient's mouth so that the shape of the existing dentition together with the gingiva is available in the form of a digital data record. A model is then made generatively according to this digital data record by layering, for example. Here again, there is a gap at the location where the patient is missing a tooth in his mouth, so the dental technical must create a model tooth at this location or a group of model teeth in the dental model thereby generated.

In a second method, gingival masks are traditionally produced on plaster models in a complex manual procedure. This procedure is a disadvantage inasmuch as the entire dental model must be handled by the dental technician when making the model tooth. In fabrication of a model tooth, in particular a model implant of a tooth or a group of teeth, this causes the shaping of this model to be extremely difficult and even inadequate in many cases.

OBJECTS OF THE INVENTION

It is therefore an object of the present invention to provide an improved dental model.

Another object is the provision of such an improved dental model that overcomes the above-given disadvantages, in particular that will permit facilitated fabrication of the model implant of a tooth or a group of teeth for the dental technician, such that a high precision is achieved and good processability of the model implant that is to be produced is ensured.

SUMMARY OF THE INVENTION

A dental modal for making a dental prosthesis has according to the invention a base body formed with model teeth and model gingiva and with a cutout in an edentate area and with a hole in a floor of the cutout. A plate is releasably fittable complementarily in the cutout and is formed with a hole aligned with the hole of the cutout. A gingiva mask is fittable on the plate in the cutout and is in turn formed with a hole aligned with the holes of the plate and of the cutout. A model implant insert is releasably fittable in the holes of the mask, plate, and cutout and carries a model implant or an implant-screw is mockup.

In other words, the present invention proposes that a cutout be provided in the area in which the model implant of the tooth or group of teeth is to be formed, and into which a plate with a gingival mask is inserted; a model implant insert comprising one or more parts can be detachably inserted into a guide hole in the cutout, in which a model implant or an implant screw mockup made of a suitable material is held, the plate having a recess for pushing through the model implant and for attaching the model implant or an abutment for it on the model implant insert.

According to this embodiment, a cutout is to be provided in the dental model in the area in which the model implant of a tooth or a group of teeth is to be formed. This cutout serves to receive a plate with a gingival mask, such that a guide hole to receive a model implant insert is also provided in this area. These parts, in particular the plate with the gingival mask are recreated according to the original model, that is the corresponding area of the jaw or dentition of the patient, so that a dental model that is faithful to the original is created by the corresponding parts in the cutout. In order for the dental technician to be able to construct the model implant, the plate and the model implant insert, into which the corresponding abutment is also introduced, may be taken out. This subassembly may then be used by the dental technician to create the model of a tooth or a group of teeth and can be handled without the dental technician being hindered by the much larger overall dental model. After complete modeling, the model together with the plate and the model implant insert can then be inserted back into the dental model, so that the overall impression and overall design of the dental model can be seen. The work of the dental technician is greatly simplified here because the parts that serve to model the model tooth or the group of model teeth, can be removed from the dental model until completing the corresponding modeling. Then these parts can be incorporated back into the dental model.

It is preferably provided here that the model implant/the model implant insert holds an implant screw mockup to which an abutment can be attached, and onto which a model implant, such as a crown can be created.

It is especially preferably provided that the plate is adapted to the cutout in such a way that an unambiguous arrangement of the plate in the cutout without any possibility of reversal or misalignment is achieved.

For example, the cutout may have a certain shape and the plate is complementarily shaped so that the plate can fit in only one position in the cutout.

To ensure the positioning and the arrangement without any mix-up, it is also possible to provide for the cutout to have a connector element or a recess and for the plate to have a hole which fits the connector element or to have a connector element which fits the recess, in which case these parts engage in one another in the ideal position.

It is also possible to provide that the plate is designed in one piece with the gingival mask.

It is preferably provided that the plate is made of a material having dimensional stability, and the gingival mask is made of an elastic material, such that the gingival mask is bonded to the plate in the ideal position.

The plate and the gingival mask here are made of different materials, the plate being made of a material having dimensional stability and the gingival mask being made of an elastic material to approximately simulate the behavior of the gingival tissue, which is advantageous in constructing the dental model.

In addition, it is preferably provided that the hole in the plate and/or the gingival mask tapers conically from the outside to the bottom of the recess and/or in the opposite direction.

Furthermore, it is especially preferably provided that the model implant insert consists of two parts in the form of half shells which have a shape-adapted recess for an implant screw mockup and hold the latter immovably in the assembled position.

This simplifies the guidance of the individual parts and the fitting of the implant screw/the implant screw mockup and ensures the alignment in the ideal position.

Furthermore, for an arrangement that is free of mix-ups it is preferably provided that the model implant insert has a polygonal outer circumference contour and the guide hole has the same cross-sectional shape.

Finally, the base with the cutout, the plate and the gingival mask, that is all of the parts manufactured generatively, being built up layer by layer to precisely match the model corresponding to the original shape on the basis of a data record taken from the patient.

BRIEF DESCRIPTION OF THE DRAWING

The above and other objects, features, and advantages will become more readily apparent from the following description, reference being made to the accompanying drawing whose sole figure is an exploded perspective view of the invention.

DETAILED DESCRIPTION

The drawing shows a dental model generally used as a working model and as a control model for producing a dental prosthesis. This dental model consists of a U-shaped base $1a$ formed with model teeth 5 and a gingiva model 6 and designed with at least one guide hole 1b for receiving a dental stump or in particular for receiving a model implant insert $2a$, $2b$ as well as having at least one connector or spring element $1c$, here a cylindrical pin, for guiding and securing parts that can be attached to the insert $2a$, $2b$. The base $1a$ has a cutout $1d$ visible at the right front in the drawing and formed by a pair of substantially perpendicular planar faces, although for another application, for instance an incisor implant job, it could have two planar vertical side faces flanking a planar horizontal floor. This cutout $1d$ is complementary to a plate $3a$ adapted to fit in it. This design allows the plate $3a$ to be removed from the base $1a$ to simplify making the dental model.

The invention also comprises the single-part or multipart model implant insert $2a$, $2b$ that makes it possible for model implants or other implant screw mockups made of plastic, ceramic or metal to be embedded and/or clamped in place. Such model implants can be incorporated into the multipart implant insert $2a$, $2b$ by joining techniques or by mechanical retention, then secured in a defined position and finally fitted in the complementary guide hole $1b$ provided for this purpose with an accurate fit. Another aspect of the invention is at least the above-described plate $3a$ that can be attached by the connector $1c$ and that can be used as a support for flexible or rigid parts, for example, a gingival mask $4a$ having a tooth hole $4b$.

The plate $3a$ is formed with at least one cylindrical socket or bore $3b$ for receiving the connector or spring element $1c$ to ensure accurate positioning of the plate $3a$ on the base $1a$ in the complementary cutout $1d$. In addition, the plate $3a$ has a borehole or recess $3c$ for inserting the model implant or parts thereof. Thus the attachment of the plate $3a$ to the base is made possible by using the model implant insert $2a$, $2b$ and the model implant. An additional part of the model the gingival mask $4a$, preferably made of a flexible material. This gingival mask $4a$ might be designed in one piece with the plate $3a$ if the materials are identical, but it is preferably made of another material, in particular a flexible material, in which case it may then be attached to the plate $3a$ in the ideal position by mechanical retention. The gingival mask $4a$ also has the hole $4b$ for insertion of a model implant. This hole $4b$ tapers in a conical shape toward the bottom side, so that the insertion of model implants is facilitated. The mask $4a$ also has an inset forming a downwardly extending projection $4c$ that fits within an upwardly projecting rim $3d$ of the plate $3a$ All the parts of the dental model are especially preferably made generatively, at least the base $1a$, the plate $3a$ and the gingival mask $4a$, so that the shape of the model is faithful to the original. For example, methacrylate or an epoxy resin may be the material for the base $1a$ and the plate $3a$. A suitable elastomeric material may preferably be considered as the material for the separate gingival mask $4a$. An implant screw mockup is preferably embedded in the model implant insert $2a$, $2b$. Then a so-called abutment can be placed, so that the corresponding crown or the dental group can be constructed on the abutment by the dental technician.

Due to the design according to the invention, work is greatly facilitated for the dental technician, while nevertheless an extremely high precision is achieved in fabrication of individual parts generatively in particular, and on the whole, the precision of the digital process chain for creating the dental model is preserved.

The invention is not limited to the illustrated embodiment but can be varied in a variety of ways within the context of the disclosure.

All new individual features and combination features disclosed in the description and/or the drawing shall be regarded as essential to the invention.

We claim:

1. A dental model for making a dental prosthesis, the model comprising:
   a base body formed with model teeth, model gingiva, a cutout in an edentate area, and a hole in a floor of the cutout;
   a plate releasably fittable complementarily in the cutout and formed with a hole aligned with the hole of the cutout;
   a gingiva mask fittable on the plate in the cutout and formed with a tooth hole aligned with the holes of the plate and of the cutout;
   a model implant insert releasably fittable in the holes of the mask, the plate, and the cutout and carrying a model implant or an implant-screw mockup of the same cross-sectional shape as the hole in the base body.

2. The dental model defined in claim 1, wherein the model implant insert holds the implant-screw mockup to which an abutment is securable on which a crown can be built.

3. The dental model defined in claim 2, wherein the cutout and the plate are shaped so as to only fit together in one position.

4. The dental model defined in claim 3, wherein the cutout and the plate have confronting faces one of which is formed with a socket and the other of which is formed with a projection engaging complementarily in the socket.

5. The dental model defined in claim 1, wherein the plate is formed of a rigid material and the mask is formed of an elastically flexible material.

6. The dental model defined in claim 1, wherein the hole of the gingiva mask or of the plate tapers frustoconically.

7. The dental model defined in claim 1, wherein the insert is formed of two parts that fit together to form a socket in which the implant-screw mockup is receivable.

8. The dental model defined in claim 1, wherein at least a lower portion of the model implant is of polygonal cross section and the hole of the cutout is of complementary shape.

* * * * *